United States Patent [19]

Meul

[11] Patent Number: 5,258,523

[45] Date of Patent: Nov. 2, 1993

[54] PROCESS FOR THE PRODUCTION OF 2-ARYL-2H-1,2,3-TRIAZOLES

[75] Inventor: Thomas Meul, Visp, Switzerland

[73] Assignee: Lonza Ltd., Gampel/Valais, Switzerland

[21] Appl. No.: 902,724

[22] Filed: Jun. 23, 1992

[30] Foreign Application Priority Data

Jun. 28, 1991 [CH] Switzerland ............... 1920/91

[51] Int. Cl.$^5$ ................................. C07D 249/06
[52] U.S. Cl. ............................................. 548/255
[58] Field of Search ................................ 548/255

[56] References Cited

FOREIGN PATENT DOCUMENTS 0350237 1/1990 European Pat. Off. .
3012193 10/1980 Fed. Rep. of Germany .
3106598 12/1981 Fed. Rep. of Germany .
642611 4/1984 Switzerland .

OTHER PUBLICATIONS

Methods of Organic Chemistry, Houben-Weyl, 4th Ed., vol. X/3, (1965), pp. 12 to 64.

Primary Examiner—Patricia L. Morris
Attorney, Agent, or Firm—Fisher, Christen & Sabol

[57] ABSTRACT

4-Akylthiomethyl-2-aryl-2H-1,2,3-triazoles and 4-arylthiomethyl-2-aryl-2H-1,2,3-triazoles are produced from γ-chloroacetoacetyl chloride, aryldiazonium salts and thiolates. In a first step, the aryldiazonium salt is reacted with the chloroacetoacetyl chloride to the corresponding 3-chloropyruvaldehyde-arylhydrazone, which is converted with the thiolate into the corresponding 3-alkylthio or 3-arylthiopyruvaldehyde-arylhydrazone. The 3-alkylthio or 3-arylthiopyruvaldehyde-arylhydrazone is cyclized with hydroxylamine-O-sulfonic acid to the desired 2-aryl-2H-1,2,3-triazole.

18 Claims, No Drawings

PROCESS FOR THE PRODUCTION OF 2-ARYL-2H-1,2,3-TRIAZOLES

BACKGROUND OF THE INVENTION

1. Field of the Invention

The invention relates to a new process for the production of 2-aryl-2H-1,2,3-triazoles.

2. Background Art

2-Aryl-2H-1,2,3-triazoles, especially those in which the triazole ring has a substituent in the 4 position, have insecticidal and acaricidal effects [European Published Patent Application No. 350237].

A known process for their production starts from arylhydrazones of α-hydroxyiminoaldehydes or -ketones, which are cyclized with oxidizing agents, such as, copper sulfate. The thus-obtained N-oxide can be reduced in a known way. The necessary hydroxyimino-arylhydrazones can be produced by reaction of the corresponding arylhydrazine with the corresponding α-dicarbonyl compound and oximation of the thus-obtained α-carbonyl-arylhydrazone. The process is laborious and, because of the oxidation and reduction steps in the course of the synthesis and in the production of the arylhydrazine necessary as an initial material, exhibits other drawbacks, especially the one that the process results in a great amount of waste.

If the hydroxyimino-arylhydrazone is first acylated the thus-obtained acyloxyimino-arylhydrazone can also be converted directly into the desired triazole by adding a base so that the formation of the N-oxide and its reduction are avoided. However, instead as when the base is used for cyclization, a salt of the carboxylic acid corresponding to the acyl group accumulates as waste.

BROAD DESCRIPTION OF THE INVENTION

The main object of the invention is to provide a simple and economical synthesis process, which has good yields and small amounts of waste, for the production of 4-substituted 2-aryl-2H-1,2,3-triazoles of the general formula:

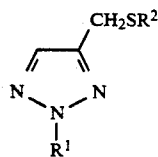

wherein $R^1$ means an optionally substituted aryl or heteroaryl group and $R^2$ means an optionally branched and/or substituted alkyl, cycloalkyl, arylalkyl (or aralkyl) or aryl group. Other objects and advantages of the invention are set out herein or are obvious herefrom to one skilled in the art.

The objects and advantages of the invention are achieved by the process and the intermediate of the invention.

The invention involves a process for the production of 2-aryl-2H-1,2,3-triazoles of the general formula:

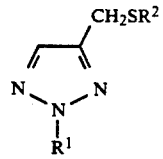

wherein $R^1$ is an optionally substituted aryl or heteroaryl group and $R^2$ is an optionally branched and/or substituted open chain or cyclic alkyl group, or an optionally substituted arylalkyl group, aryl group or heteroaryl group. γ-Chloroacetoacetyl chloride:

$$ClCH_2CCH_2COCl \quad \text{II}$$
$$\underset{\|}{O}$$

in a first step, is coupled with a diazonium salt of the general formula:

wherein $R^1$ has the above-mentioned meaning, n is 1 to 2, preferably 1, and $A^{n-}$ is an anion of a monobasic or multibasic strong acid, to the corresponding 3-chloropyruvaldehyde arylhydrazone of the general formula:

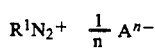

wherein $R^1$ has the above-mentioned meaning, in a second step, the 3-chloropyruvaldehyde arylhydrazone of the general formula IV is reacted with a thiolate of the general formula:

wherein $R^2$ has the above-mentioned meaning, m is 1 to 3 (depending on the valence of the cation employed), preferably 1, and $Y^{m+}$ is an inorganic or organic cation, to the corresponding 3-substituted pyruvaldehyde arylhydrazone of the general formula:

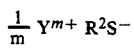

wherein $R^1$ and $R^2$ have the above-mentioned meaning, and finally, in a third step, the 3-substituted pyruvaldehyde arylhydrazone of the general formula V is cyclized with hydroxylamine-O-sulfonic acid to one of the 2-aryl-2H-1,2,3-triazoles of the general formula I.

Preferably a diazonium salt wherein $R^1$ is an optionally substituted phenyl group is used. Preferably a diazonium salt wherein $A^{n-}$ is chloride or hydrogen sulfate is used. Preferably the diazonium salt is produced by diazotization of the corresponding amine with nitrosylsulfuric acid. Preferably a sodium alkylthiolate is used as the thiolate. Preferably the reaction of 3-chloropyruvaldehyde-arylhydrazone is performed with the thiolate at 0° to 40° C. in a protic or polar aprotic solvent. Preferably the cyclization is performed with hydroxylamine-O-sulfonic acid in an aqueous organic solvent system, in that the substituted pyruvaldehyde-arylhydrazone is reacted first with sulfonic acid at a temperature below 40° C. and then the pH of the reaction mixture is adjusted with a base to a value of 6 to 8 and the mixture is optionally heated to a temperature up to 80° C. Preferably an acetonitrile-water mixture is used as the aqueous-organic solvent system. Preferably 2,6-dichloro-4-trifluoronethyl-benzenediazonium hydrogen sulfate is used as the diazonium salt.

The invention also includes 3-chloropyruvaldehyde-1-[2,6-dichloro-4-(trifluoromethyl)-phenyl]hydrazone.

DETAILED DESCRIPTION OF THE INVENTION

It was found that the γ-chloroacetoacetyl chloride, obtainable in a way known in the art (Swiss Patent No. 642,611) from diketene and chlorine, can be converted with aryldiazonium salts directly to the corresponding 3-chloropyruvaldehyde-arylhyrazones in the sense of a Japp-Klingemann reaction while obtaining the chloromethyl group.

It was known that γ-chloroacetoacetic acid, obtainable by hydrolysis from the acid chloride or corresponding esters, can be reacted in the presence of a base with diazotized haloanilines to 3-chloropyruvaldehyde halophenylhydrazones [German OS No. 3,012,193]. However, γ-chloroacetoacetic acid has little stability as a β-ketocarboxylic acid and easily decarboxylates to chloroacetone. On the other hand, the process according to the invention gets by without adding a base and requires no separate hydrolysis step. Thus, even the danger of a decomposition of the γ-chloroacetoacetic acid is eliminated.

In this case, as the aryldiazonium salts, basically all diazonium salts obtainable by the diazotization of unsubstituted or substituted primary, monocyclic or polycyclic aromatic amines according to known methods can be used [see, e.g., "Methoden der Organischen Chemie" (Methods of Organic Chemistry), Houben-Weyl, 4th edition, Vol. X/3, (1965), Thieme Verlag, Stuttgart, pages 12 to 64]. Preferably the diazotization is performed with nitrosylsulfuric acid, since in such manner diazotization in an organic solvent, such as, glacial acetic acid, is possible while no great excess of mineral salt is necessary and no inorganic salt is involved. Of course, diazotization can also be performed according to the usual method with aqueous hydrochloric acid or sulfuric acid and sodium nitrite, however, then the above-mentioned additional advantages are absent. Especially preferred is the diazotization with nitrosylsulfuric acid in acetic acid, which is diluted with water after completion of the diazotization.

Advantageously, the γ-chloroacetoacetyl chloride is used in dissolved form, for example, in the form of dichloromethane solution resulting in the production according to Swiss Patent No. 642,611. In the coupling with the diazonium salt, the acid chloride group is hydrolyzed from the present water to the carboxylic acid group and then is decarboxylated, so that HCl, $CO_2$ and the acid of the diazonium salt, such as, sulfuric acid, result as by-products.

The chloromethyl group of 3-chloropyruvaldehyde-arylhyrazone is suitably reacted with a thiolate. As thiolates, alkylthiolates or arylthiolates (thiophenolates) are especially suitable. Advantageously the thiolates are obtained by deprotonation of the corresponding thioles with bases. But for thioles of low acidity strong bases, for example, alkali alcoholates, in the corresponding alcohols are suitably used as solvents; while for stronger acidic thioles, such as, thiophenols, also less strong bases, for example trialkylaminesin polar aprotic solvents such as acetonitrile, are used. The reaction of the thiolate with the chlorohydrazone is preferably performed at a temperature of 0° to 40° C.

The correspondingly substituted pyruvaldehyde-arylhydrazone is then cyclized with hydroxylamine-O-sulfonic acid, as known from German OS No. 3,106,598—the reaction conditions described there are also suitable for the process according to the invention.

According to the process of the invention, a large number of different products can be produced depending on the aryldiazonium salt or the arylamine on which it is based and the nucleophile used. Especially preferred among the classes or compounds already mentioned are: diazonium salts of the anilines and substituted anilines, such as, o-, m- and p-toluidine, o-, m- and p-chloroaniline, o-, m- and p-nitroaniline, o-, m- and p-anisidine, the various isomeric xylidines and dichloroanilines, side-chain halogenated alkylanilines such as p-trifluoromethylaniline, mixed substituted anilines such as chlorotoluidine, nitrotoluidine or dichlorotrifluoromethylanilines, especially 2,6-dichloro-4-trifluoromethylaniline, or diazonium salts of bicyclic and polycyclic amines, such as, aminobiphenyls and α- and β-naphthylamine.

As nucleophiles especially preferred are alkali-lower alkylthiolates, i.e., alkali salts of lower alkylmercaptans, especially with sodium as the alkali metal, i.e., for example, of methanethiolate, ethanethiolate, 1-propanethiolate and 2-propanethiolate, and the alkali salts of various isomeric butylmercaptans, especially preferred, sodium methanethiolate.

The following examples illustrate the performance of the process according to the invention.

EXAMPLE 1

3-Chloropyruvaldehyde-1-[2,6-dichloro-4-(trifluoromethyl)phenyl]-hydrazone 144.3 g of 4-(trifluoromethyl)-2,6-dichloroaniline (96 percent) was dissolved in 120 ml of acetic acid and mixed within one hour at 20° C. with 209.7 g of nitrosylsulfuric acid (40 percent in sulfuric acid monohydrate). Then the reaction mixture was cooled to 0° C. and diluted with 480 ml of water. This solution was instilled in a solution of 111.6 g of γ-chloroacetoacetyl chloride in 400 ml of dichloromethane (produced according to Swiss Patent No. 642,611) at −5° to 0° C. within one hour. The mixture was stirred for one more hour at 10° C., and then the phases were separated. The aqueous phase was extracted with 100 ml of dichloromethane, the combined organic phase concentrated by evaporation and the residue suspended with 300 ml of cyclohexane. The undissolved solid was filtered off, washed two times each with 100 ml of cyclohexane and dried at 40 torr. The yield of the product was 183.6 g of ochre crystals. Data concerning the product was:

$^1$H-NMR (CDCl$_3$, 300 MHz) δ: 4.68 (s,2H), 7.32 (s,1H) 7.65 (s,2H), 8.56 (br.s,1H).

MS(EI, 70 eV):

m/z 332 (M$^+$, 35 percent, isotope distribution corresponding to 3Cl):

283 (16), 224 (100, 2Cl),
201 (24), 166 (40), 119 (22),
96 (41), 77 (25).

EXAMPLE 2

3-(Methylthio)pyruvaldehyde-1-[2,6-dichloro-4-(trifluoromethyl)phenyl]hydrazone 9.2 g of sodium was dissolved in 900 ml of methanol. 21.3 g of methanethiol was introduced into the sodium methylate solution thus obtained. Then 110.0 g of 3-chloropyruvaldehyde-1-[2,6-dichloro-4-(trifluoromethyl)-phenyl]hydrazone (produced according to Example 1) was added in portions at 30° to 40° C. The reaction mixture was stirred for 1 hour at 40° C. and then the methanol was distilled off in a water jet vacuum. The residue was mixed with 500 ml of water and extracted three times with 250 ml of dichloromethane each. The combined dichloromethane extracts were dried on sodium sulfate and concentrated by evaporation. The residue was suspended in 200 ml of n-hexane, filtered off and dried in a water jet vacuum. The yield of the product was 92.2 g [content (GC): 94.7 percent]. The melting point of the product was 88° to 90° C.

EXAMPLE 3

2-[2,6-Dichloro-4-(trifluoromethyl)phenyl]-4-(methylthiomethyl)-2H-1,2,3-triazole 5.25 g of 3-(methylthio)pyruvaldehyde-1-[2,6-dichloro-4-(trifluoromethyl)phenyl]hydrazone (produced according to Example 2) was dissolved in 75 ml of acetonitrile/water (4:1) and mixed with 2.36 g of hydroxylamine-O-sulfonic acid (93.4 percent). The reaction mixture was stirred 1 hour at 30° C. and then adjusted to a pH of 8 by addition of 20 ml of saturated aqueous sodium bicarbonate solution and heated 5 hours to 70° C. After cooling to room temperature, the acetonitrile was distilled off in a water jet vacuum and the remaining aqueous solution wa extracted two times with 25 ml of dichloromethane each. The combined dichloromethane phases were dried on sodium sulfate and concentrated by evaporation. 4.6 g of crude product with a content (HPLC) of 63.4 percent was obtained as a residue. For purification the crude product was recrystallized hot from 22 ml of isopropyl alcohol. The yield of the product was 2.3 g [content (HPLC): 93.3 percent].

What is claimed is:

1. A process for the production of a 2-aryl-2H-1,2,3-triazole of the formula:

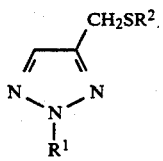

wherein $R^1$ is a member selected from the group consisting of phenyl, o-methylphenyl, m-methylphenyl, p-methylphenyl, o-chlorophenyl, m-chlorophenyl, p-chlorophenyl, o-nitrophenyl, m-nitrophenyl, p-nitrophenyl, o-methoxyphenyl, m-methoxyphenyl, p-methoxyphenyl, a dimethylphenyl, a dichlorophenyl, a chloromethylphenyl, a nitromethylphenyl, a side-chain halogenated alkylphenyl, and a dichloro-trifluoromethylphenyl, and $R^2$ is a member of the group consisting of a branched alkyl group, an open chain alkyl group and a cyclic alkyl group, characterized in that γ-chloroacetoacetyl chloride:

in a first step, is coupled with a diazonium salt of the formula:

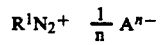

wherein $R^1$ has the above-mentioned meaning, n is 1 to 2, and $A^{n-}$ is an anion of a monobasic strong acid or a multibasic strong acid, to the corresponding 3-chloropyruvaldehyde arylhydrazone of the formula:

wherein $R^1$ has the above-mentioned meaning, in a second step, the 3-chloropyruvaldehyde arylhydrazone of the formula IV, is reacted with a thiolate of the formuls:

wherein $R^2$ has the above-mentioned meaning, and $Y^+$ is hydrogen or an alkali metal cation, to the corresponding 3-substituted pyruvaldehyde arylhydrazone of the formula:

wherein $R^1$ and $R^2$ have the above-mentioned meaning, and, finally, in a third step, 3-substituted pyruvaldehyde arylhydrazone of the formula V is cyclized with hydroxylamine-O-sulfonic acid to said 2-aryl-2H-1,2,3-triazole of the formula I.

2. The process according to claim 1 wherein $R^1$ is 2,6-dichloro-4-trifluoromethyl-phenyl.

3. The process according to claim 1 wherein a diazonium salt wherein $A^{n-}$ is chloride or hydrogen sulfate, is used.

4. The process according to claim 3 wherein the diazonium salt is produced by diazotization of the corresponding amine with nitrosylsulfuric acid.

5. The process according to claim 4 wherein a sodium alkylthiolate is used as the thiolate.

6. The process according to claim 5 wherein a methanethiolate is used as the thiolate.

7. The process according to claim 6 wherein the reaction of 3-chloropyruvaldehyde-arylhydrazone is performed with the thiolate at 0° to 40° C. in a protic or polar aprotic solvent.

8. The process according to claim 7 wherein the cyclization is performed with hydroxylamine-O-sulfonic acid in an aqueous organic solvent system, in that the substituted pyruvaldehyde-arylhydrazone is reacted first with sulfonic acid at a temperature below 40° C. and then the pH of the reaction mixture is adjusted with a base to a value of 6 to 8 and the mixture is optionally heated to a temperature up to 80° C.

9. The process according to claim 8 wherein an acetonitrile-water mixture is used as the aqueous-organic solvent system.

10. The process according to claim 9 wherein 2,6-dichloro-4-trifluoro-methylbenzenediazonium hydrogen sulfate is used as the diazonium salt.

11. The process according to claim 1 wherein the diazonium salt is produced by diazotization of the corresponding amine with nitrosylsulfuric acid.

12. The process according to claim 1 wherein a sodium alkylthiolate is used as the thiolate.

13. The process according to claim a methanethiolate is used as the thiolate.

14. The process according to claim 1 wherein the reaction of 3-chloropyruvaldehyde-arylhydrazone is performed with the thiolate at 0° to 40° C. in a protic or polar aprotic solvent.

15. The process according to claim 1 wherein the cyclization is performed with hydroxylamine-O-sulfonic acid in an aqueous organic solvent system, in that the substituted pyruvaldehyde-arylhydrazone is reacted first with sulfonic acid at a temperature below 40° C. and then the pH of the reaction mixture is adjusted with a base to a value of 6 to 8 and the mixture is optionally heated to a temperature up to 80° C.

16. The process according to claim 15 wherein an acetonitrile-water mixture is used as the aqueous-organic solvent system.

17. The process according to claim 1 wherein 2,6-dichloro-4-trifluoro-methylbenzenediazonium hydrogen sulfate is used as the diazonium salt.

18. The process according to claim 1 wherein n is 1 and m is 1.

* * * * *